US012678559B2

(12) United States Patent
Rytz

(10) Patent No.: US 12,678,559 B2
(45) Date of Patent: Jul. 14, 2026

(54) DRUG DELIVERY DEVICE WITH AN IMPROVED MECHANISM FOR CONTROLLING THE DELIVERY RATE

(71) Applicant: Ypsomed AG, Burgdorf (CH)

(72) Inventor: Bernhard Rytz, Zollbrück (CH)

(73) Assignee: Ypsomed AG, Burgdorf (CH)

( * ) Notice: Subject to any disclaimer, the term of this patent is extended or adjusted under 35 U.S.C. 154(b) by 972 days.

(21) Appl. No.: 17/902,715

(22) Filed: Sep. 2, 2022

(65) Prior Publication Data

US 2022/0409809 A1 Dec. 29, 2022

Related U.S. Application Data

(63) Continuation of application No. PCT/EP2021/054478, filed on Feb. 24, 2021.

(30) Foreign Application Priority Data

Mar. 4, 2020 (EP) ..................................... 20160889

(51) Int. Cl.
*A61M 5/142* (2006.01)
*A61M 5/145* (2006.01)
(Continued)

(52) U.S. Cl.
CPC ........ *A61M 5/14566* (2013.01); *A61M 5/172* (2013.01); *H02P 25/03* (2016.02); *A61M 2205/3317* (2013.01)

(58) Field of Classification Search
CPC .......... A61M 5/14248; A61M 5/14566; A61M 5/172
See application file for complete search history.

(56) References Cited

U.S. PATENT DOCUMENTS 3,739,943 A 6/1973 Wilhelmson et al.
4,024,864 A * 5/1977 Davies ................... A61M 5/172
128/DIG. 7
(Continued)

FOREIGN PATENT DOCUMENTS

CN 2534721 Y * 2/2003
EP 3260149 A1 12/2017
(Continued)

OTHER PUBLICATIONS

Xu CN 2534721 Y machine translation (Year: 2003).*
(Continued)

*Primary Examiner* — Laura A Bouchelle
(74) *Attorney, Agent, or Firm* — Dorsey & Whitney LLP

(57) ABSTRACT

A drug delivery device including a reservoir configured to contain a fluid to be delivered by advancing a piston in the reservoir at an advancement speed defining a delivery rate for the medicament. The device further includes an electric motor configured to drive the delivery mechanism by rotation to advance the piston at the advancement speed. The device further includes a control unit that controls a rotational speed and an on state/off state of the electric motor. The control unit determines rotational speed of the electric motor based on a back-electromagnetic force signal provided from the electric motor while operating in a monitoring mode. The control unit controls the rotational speed of the electric motor such that a back-emf signal can be detected in the monitoring mode. The control unit modulates the on state/off state of the electric motor to adjust the delivery rate of the medicament.

14 Claims, 4 Drawing Sheets

(51) Int. Cl.
   _A61M 5/172_      (2006.01)
   _H02P 25/03_      (2016.01)

(56)                References Cited

U.S. PATENT DOCUMENTS

2007/0033103  A1    2/2007  Collins et al.
2008/0294098  A1   11/2008  Sarkinen et al.
2011/0084635  A1    4/2011  Brown

FOREIGN PATENT DOCUMENTS

EP        3539592  A1   9/2019
EP        3875127  A1   9/2021
WO     2007033103  A1   3/2007
WO     2011044706  A1   4/2011
WO     2021175668  A1   9/2021

OTHER PUBLICATIONS

Extended European Search Report issued in European Patent Application No. 20160889.0, mailed on Jul. 29, 2020, 12 pages.
International Search Report and Written Opinion issued in International Application No. PCT/EP2021/054478, mailed on May 14, 2021, 15 pages.

* cited by examiner

DRUG DELIVERY DEVICE WITH AN IMPROVED MECHANISM FOR CONTROLLING THE DELIVERY RATE

CROSS-REFERENCE TO RELATED APPLICATIONS

This application claims priority to International Patent Application No. PCT/EP2021/054478, filed Feb. 24, 2021, entitled "DRUG DELIVERY DEVICE WITH AN IMPROVED MECHANISM FOR CONTROLLING THE DELIVERY RATE," which in turn claims priority to European Application No. 20160889.0, filed Mar. 4, 2020, entitled "DRUG DELIVERY DEVICE WITH AN IMPROVED MECHANISM FOR CONTROLLING THE DELIVERY RATE", each of which is incorporated by reference herein, in their entirety and for all purposes.

TECHNICAL FIELD

The current disclosure relates to an injection device for drug delivery. In particular, this disclosure relates to improved monitoring of a state of the electric motor of the injection device using aback-electromagnetic force (back-emf) signal.

BACKGROUND

Injection and infusion devices are used for subcutaneous or intravenous (IV) delivery of liquid medicaments to a patient to treat a wide variety of diseases such as auto immune diseases, chronic diseases such as diabetes, cancer or hormone deficiencies.

Infusion devices may deliver the medication from a reservoir using a drive mechanism and a control mechanism that controls the advancement of a piston rod that abuts a moveable plunger present in the reservoir containing the medication. The medication is delivered to the patient via a fluid path and an external infusion set including a needle for subcutaneous delivery. With such infusion devices both continuous and intermittent medicament delivery profiles can be programmed.

An injection device delivers the medication from a reservoir or a pre-filled syringe (PFS) using a drive mechanism for advancing a piston in the reservoir or PFS to expel the medication via a needle that is attached or is attachable to the injection device. Injection devices may be used for delivery of a single dose, such as a fixed dose or a variable dose. Injection devices may be designed for delivery of multiple single doses.

A patch device is an example of an infusion or an injection device that is attachable to the skin of the patient. Such patch devices may not need an external infusion set for delivery, as the needle is directly contained in the patch device and may be inserted into the patient therefrom.

Depending on the therapy, the delivery rate for a medicament may vary. For example, in diabetes treatment, a relatively low basal rate is delivered by an infusion device throughout the day and night and bolus injections are given for each meal. Even for an injection device solely delivering a bolus of a medicament (e.g., a bolus injector), the delivery rate and volume may change based on age or severity of the disease. During therapy for a patient, it may be determined that the delivery rate of the medicament should be changed, as modern medicaments may require specific and time dependent dosage regimes. Additionally, therapies that are based on high viscous medicament (e.g., based on large molecules retrieved from recombinant DNA sources) may require delivery at a low rate, as otherwise the injection may be accompanied by pain or the patient's body may not be capable to absorb the viscous medicament. The therapy may be interrupted due to an adverse event, and consequently, the intended amount of medication cannot be delivered.

The drive mechanism for driving the piston rod in the injection or infusion device may be driven purely mechanical (e.g., using a coil or leaf spring), by hydraulic (osmotic) pressure, by a pneumatic source, or by an electric source. The latter may be a volumetric change of a galvanic cell or using an electric motor. An advantage of using an electric motor is that the rotational speed may be varied easily and thereby allowing better control of the delivery rate compared to, for example, the purely mechanical or osmotic power sources. An advantage of using an electric motor is that a gearing can be positioned between the motor and the delivery mechanism to gear up or gear down the rotational speed (or torque). Especially in combination with a device platform, which is adapted to treat diseases using a variety of delivery rates and viscosities of the medicament, the use of an electric motor (with or without a gearing) may be an attractive solution since different delivery rates can be selected for a single design of the device. The selection of the delivery rate may be done at the factory (pharmaceutical company) or by the patient. Additionally, an interruption of the delivery rate during therapy may occur. For example, an occlusion in a fluid delivery path or a mechanical blocking of the delivery mechanism. The monitoring of the drive mechanism and detection of adverse events that may interrupt medicament delivery is thus important for a safe treatment therapy.

An example of a patch device is presented in EP3539592A1 disclosing a patch delivery device with a bottom housing part, a capacitive sensor, an adhesive patch with a first adhesive layer contacting the bottom housing part and a second adhesive layer for contacting the skin of a patient, and a release liner made of coated paper or a thin sheet of plastic that covers the second adhesive layer prior to use of the device. Exemplary sub-assemblies and components of the patch delivery device include a cartridge retainer, a needle insertion mechanism for inserting a cannula into the skin of the patient, a fluid path for connecting the cannula to the cartridge, and a drive mechanism for dispensing the liquid and including an electric motor and a battery. These patch injection devices may be suitable for injectable liquids with a high viscosity of at least 1, in some examples. In other examples, the patch injection devices may be suitable for injectable liquids with a high viscosity of at least 15, or at least 50 cP ($0.050\ \mathrm{kgm^{-1}s^{-1}}$) in yet other examples. The rotational speed of the electric motor may be monitored using a sensor, for example, using an encoder. In a sensor-less configuration, no extra rotor position sensor is provided, and the rotation of the rotor is monitored from measurements of a back electromagnetic force (back-emf) at the terminals of the stator coils. An arrangement for a driver circuit using the back-emf signal for monitoring the rotational speed of the electric motor is presented in application EP 19176233.5.

A problem using the back-emf signal to monitor the rotational speed of an electric motor is described in U.S. Pat. No. 4,896,085. The back-emf signal that is normally created at high rotational speeds may not be not present yet at low rotational speeds. This is especially important when the volumetric delivery rates for the medicament are low since this requires also low rotational speeds for the electric motor. Additionally, the transition from a rotating electric motor to non-rotating motor caused by an adverse event may include a reliable detection of the presence or absence of a back-emf signal prior to the adverse event.

SUMMARY

Embodiments described in this disclosure overcome the aforementioned drawbacks and provide a drug delivery device that may be driven by an electric motor with sensorless detection and control of the rotational speed. The drug delivery device may accurately deliver the medicament at low delivery rates, while monitoring the rotational speed using back-emf to obtain a reliable, low cost control of the delivery rate.

The drug delivery device may include a housing including a wall separating the internal parts or units from the ambient and providing mechanical support. The wall may be part of a sterile barrier. The housing may have a pen-shape or an elongated flattened shape configured to be attached or worn on the body of a patient. The housing having an elongated or flattened shape may have a bottom housing part for attachment to the body using an adhesive layer. The adhesive layer may include at least two adhesive layers, one for contacting the housing and the other for contacting the skin. The adhesive layer may extend beyond the lateral dimensions of the housing. The skin adhesive layer may be covered before use by a protective release liner. The housing may further includes a top housing part, which may include an actuation button and optical indicators that are located behind the wall. The bottom or top housing part may have a viewing window for viewing optical indicators and/or a reservoir including the medicament. The housing may have a removable cover that is configured to close an opening in the housing intended for receiving the reservoir. The cover may be configured to close a reservoir holder adapted to hold and fixate the reservoir in the delivery device. The cover may have the viewing window. The delivery device may be ready to use, e.g., the reservoir with the medicament may be present in a closed device or the reservoir may be inserted prior to use through the opening in the housing. In the latter case, the delivery device and the reservoir with the medicament may be provided in a kit, in some examples. The delivery device may have a fluid path unit including a tubing for connecting a skin insertion needle to the medicament present in the reservoir. Optionally, the fluid path unit may include a reservoir needle that is adapted to penetrate into the reservoir (e.g., via a septum) to establish a fluid connection to the skin insertion needle via the tubing. The reservoir may have a fluid outlet or the outlet may be established via the reservoir needle. The fluid path unit may be in a sterile state during storage (e.g., over the course of the device's shelf life) prior to operating the delivery device.

The fluid path unit may have an insertion mechanism for insertion of the skin needle through an aperture in the housing into the injection site. The insertion mechanism may have a needle retraction mechanism for retracting the skin needle once the medicament has been delivered. Additionally, the insertion mechanism may also provide for the insertion of the reservoir needle into the reservoir. The delivery of the drug from the reservoir may be driven by an electric motor configured to operate a delivery mechanism, optionally via a gearing mechanism located between the electric motor and the delivery mechanism. The delivery mechanism may include a piston rod for driving a piston in the reservoir to deliver the drug through the outlet of the reservoir. The delivery device may be powered by a battery and controlled by a control unit. Optionally, a sensor system may be part of the electric circuitry to detect skin attachment or skin detachment of the device. The control unit, battery, delivery mechanism, reservoir, fluid path unit including the insertion mechanism may be located inside the housing of the device. The sensor may be located inside the housing or may be part of the adhesive layer for attaching the device to the patient.

The drug delivery device includes a reservoir containing a fluid medicament to be delivered from the device by advancing a piston in the reservoir at an advancement speed defining a delivery rate for the medicament through an outlet of the reservoir. The electric motor may drive the delivery mechanism of the drug delivery device by rotation for advancing the piston at the advancement speed (e.g., at a target advancement speed), and the control unit may be configured to control the rotational speed and/or the on/off-state of the electric motor. The rotational speed of the electric motor (e.g., rotation speed of a rotor in the electric motor), may be measured by operating the electric motor in a monitoring mode for detecting a back-electromagnetic force (back-emf) signal of the electric motor, and this signal may be sent to, or monitored by, the control unit. The control unit may control the rotational speed of the electric motor such that a back-emf signal (e.g., a reliable back-emf signal) can be detected in the monitoring mode. The control unit may further modulate the on/off-state of the electric motor to control the delivery rate (e.g., a target delivery rate) of the medicament through the outlet.

The advancement speed is typically expressed in millimeters per minute (mm/min) for linear advancement of the piston in the reservoir along the delivery direction, or along an axis defined by the reservoir. The delivery rate for the medicament may be a volumetric delivery rate expressed in milliliters per minute (ml/min). The medicament may be delivered through linear advancement of the piston to reduce the volume of the medicament contained in the reservoir such that the fluid medicament is expelled through the outlet. The delivery mechanism may include a drive train transmitting the rotation of the electric motor into advancement of the piston in the reservoir. The delivery mechanism may include a piston rod that is directly or indirectly in engagement with the piston in the reservoir. The delivery mechanism may include a gearing mechanism to gear up or gear down the rotation of the electric motor for advancing the piston in the reservoir. The piston rod may linearly advance without rotation, or advance by a combination of rotation and linear advancement (e.g., by a helical movement). The piston rod may include a threaded piston rod having an external threading engaging an internal threading of a nut member that is part of the delivery mechanism or part of the gearing mechanism. The nut member may be sleeve shaped with a threading or thread segment on the inside engaging the outside threading of the piston rod. The piston rod may further include a longitudinally oriented groove oriented parallel to the longitudinal axis of the piston rod for a splined engagement with the housing or a housing part of the drug delivery device such that the piston rod is linearly advanced as the nut member is rotated. In this example, the piston rod may linearly advance without rotation. Optionally, the groove of the piston rod is helically shaped with a pitch different from the pitch of the threaded engagement with the nut member. The groove may be splined to the housing such that rotation of the nut member advances the piston rod, which rotates as well, according to the pitch of the helical groove. Alternatively, the piston rod may be a hollow piston rod including an internal threading engaging an external threading of a drive member. The drive member may be part of, or coupled to, the drive mechanism or to the gearing mechanism. Rotation of the drive member may drive the hollow piston rod without rotation if the hollow piston rod is prevented from rotation with respect to the housing.

Optionally, the threaded piston rod is threadedly engaged with the housing and the nut member is splined to the longitudinal groove such that rotation of the nut member rotates the piston rod, which is subsequently advanced by the threaded engagement with the housing. The delivery mechanism may be driven by rotation of the electric motor and this rotation may be used to advance the piston rod at the advancement speed. The drive train of the electric motor, the delivery mechanism with or without a gearing mechanism, and a nut driving the piston rod may form a multi-part system with a certain elasticity and play, e.g., not a rigid system. For example, parts of the system may be made from a plastic material or a metal each having different elasticities, and gearing wheels or worm wheels may be designed with a certain play between two engaging parts.

In some examples, the piston rod is a single piece piston rod. Alternatively the piston rod may include a plurality of coaxially arranged sleeves forming a telescopic piston rod arrangement that may be extended for advancing the piston at the advancement speed. As another alternative, the piston rod may be segmented including segments that are linked to each other (e.g., by a film link), and the segmented piston rod may be reversibly transformed from a linear to a curved configuration.

The control unit may be located on a printed circuit board (PCB) including integrated circuits for controlling the drug delivery device, including controlling the rotational speed of the electric motor and/or the on/off state of the electric motor. An advantage of the control unit being adapted to control the rotational speed is that a wide range of delivery rates can be selected. Other units of the device that may be controlled by the control unit may be the visual and/or acoustic and/or tactile signaling units of the device. Visual signaling may be based on LED indicators. Acoustic signaling may use a load speaker. Tactile feedback may be based on a vibrating unit. The control unit may be powered by the battery and may include a memory storing a) the parameters to operate the device, such as target delivery rates, target delivery speeds, delivery times, correlations between a target rotational speed and a target delivery rate, and/or calibration data; and b) device indicators, such as the lot number or batch number, date of production, the expiration date, calibration data, the size and type of cartridge, and/or the medicament used. The control unit may also include a transmitter/receiver unit, using, for example low-energy Bluetooth®, or a direct-to-cloud technology, such as a 5G technology for wireless communication with an external device, such as a cellular phone or smart phone, and/or to a cloud service or the like.

The rotational speed of the electric motor may be defined by the number of steps per second of a rotor or a drive axle that is, or may be, coupled to the drive mechanism. For example, a stepper motor may have a defined amount of steps per rotor revolution. The rotational speed may be controlled by the control unit by varying the pulse frequency directed to the electric motor (e.g., varying the pulse frequency directed to the stator coils of the electric motor).

The on-state for the electric motor may be determined based on whether a drive axle of the electric motor is rotating. The rotation may be at a continuous rotational speed. In the on-state, the drive axle or the rotor is rotated while an electric torque is applied to the axle or the drive axle or rotor rotates due to its moment of inertia while no electric torque is applied.

The off-state for the electric motor may be detected when a drive axle or rotor of the electric motor is not rotating.

In the monitoring mode for the drug delivery device (e.g., for the electric motor that is part of the drug delivery device), the rotational speed of the electric motor may be monitored, or the number of steps-per-second may be measured while the electric motor is rotating, e.g., is in the on-state. In the on-state, the driving voltage may be interrupted or paused for a short time (e.g., less than one millisecond). The rotational speed may be measured using the back electro-magnetic force signal (back-emf) induced by the rotation of the electric motor during the interruption or pausing. An advantage of using the back-emf signal is that it uses the components of the electric motor for detecting the rotational speed and no additional parts, as compared with devices that include an encoder or an optical measuring unit to measure rotational speed of an electric motor. The back-emf signal may be generated by rotation of conductive coils in a magnetic field (which may be established by static magnets) or by rotation of static magnets in conductive coils (which are static). Such a back-emf signal may be principally generated upon relative rotation between the conductive coil and the static magnet. At a rotational speed of zero revolutions (or steps) per second, no back-emf signal is generated. However, the back emf signal may be created at higher rotational speeds and not yet present at low rotational speeds, or at least the back-emf signal cannot be reliably detected at low rotational speeds. The detection limit depends on the sensitivity of the senor unit that is part of the control unit, which may include filters, such as bandpass filters, to reduce the signal-to-noise ratio. A reliable back-emf signal may be sent to the control unit and measured by the sensor once a minimum rotational speed for the electric motor has been reached.

The control unit may control the rotational speed and modulate the on/off state of the electric motor. The on/off modulation may be established by switching the electric motor between the rotating on-state and the non-rotating off-state. The electric motor may be modulated as a function of time. e.g., the motor is in the on-state for a certain time (on-time) and in the off-state (off-time). The on/off time periods may be equal, but may also be different from another. In some examples, the off-time may be greater than the on-time to operate the delivery device at low target delivery rates. The rotational speed and the on/off modulation may be controlled to fulfill the following conditions:

i) The rotational speed may be controlled to be greater than a minimum rotational speed selected for reliable generation and detection of the back-emf signal by the control unit at any time during the on-state, and ii) The on/off modulation may be used to control the linear advancement speed (mm/min) of the piston in the cartridge, which may generate the volumetric delivery rate (ml/min) and the delivery time. The on/off modulation may be used to control the delivery rate to be at, or close to a target delivery rate.

At some low delivery rates (ml/min), the rotational speed of the electric motor may be below the minimum rotational speed selected for reliably generating and detecting a back-emf signal. That is, if the electric motor were continuously running in the on-state below the minimum rotational speed to satisfy a low delivery rate, the first condition (e.g., condition i) would not be fulfilled (e.g., the motor would be rotating at a speed that is too low for back-emf detection).

Thus, by modulating the electric motor between the on-state and off-state, the electric motor can be operated at least at the minimum rotational speed for back-emf detection (e.g., condition i) and still operate the device at low delivery rates (e.g., condition ii). By operating the delivery device at the minimum rotational speed for detecting the back-emf signal and the on/off modulation, the delivery device can be operated at low delivery rates without compromising the reliability and precision of the device.

If the specified delivery rates are such that the continuous rotational speed is above the minimum rotational speed, no on/off modulation is required and the electric motor may be continuously rotating while delivering the medicament through the outlet of the cartridge. If the targeted delivery rates are such that the rotational speed of the electric motor would be below the detection limit of a reliable back-emf signal, then the rotational speed may be set at least at the minimum rotational speed and the delivery rate may be controlled by the on/off modulation. In some examples, the device may be calibrated and/or configured in the factory to establish the relationship between the delivery rate (ml/min) and the minimum rotational speed required for the electric motor. The device may be calibrated and/or configured to operate with different types of reservoirs having different volumes.

Additionally, the reliable detection of the back-emf signal may also ensure that deviations in rotation of the electric motor can be detected, for example due to an occlusion, a mechanical blockage, or when the piston has reached the end of the reservoir.

The drug delivery device may include a piston rod that abuts the piston in the reservoir. The piston rod may be advanced at the advancement speed by the delivery mechanism.

The reservoir of the drug delivery device may include a cartridge including the piston that is linearly advanced in the cartridge by the delivery mechanism towards the outlet of the cartridge.

The cartridge may be tubular shaped including a barrel closed on one end by the piston and on the opposite end by a pierceable septum covering the outlet of the reservoir. The septum may be crimped onto a shoulder section of the cartridge. The septum may be pierced by a needle that is connected or connectable to a patient for delivery of the medicament. Alternatively, the reservoir may include a syringe closed by the piston on one end and having a stacked needle on the opposite end forming the outlet. The tip of the needle may be enclosed by a needle shield to preserve sterility of the contents of the prefilled syringe. Alternatively, the cartridge may be non-linear shaped, for example curved, to form an arc-shaped reservoir. The cartridge may be made from a rigid material such as glass, or a rigid plastic material, such as polypropylene or a cyclocolefinic copolymer (COC); and the piston may be made from a rubber, which is at least partially elastically compressed to fit into the barrel of the cartridge to provide a tight seal for the medicament. An advantage of using a linear glass cartridge including a barrel and a pierceable septum is that this is an established and well-accepted primary packaging by the pharmaceutical industry, and which can be filled on standard fill finish lines. The rigid cartridge may have a circular or an ovular cross section. Alternatively, a flexible or semi-rigid material may be used for the reservoir to form a compressible or collapsible reservoir.

The electric motor may include a brushless direct-current (DC) motor (BLDC) and the on-state is defined by the control unit directing a driving voltage to at least one of a plurality of stator coils, thereby applying a driving torque to the rotor of the BLDC motor for setting the rotor in rotation. A BLDC may include a rotor having a plurality of static magnets surrounded by a plurality of stator coils that may be coupled to a DC source via the control unit. The control unit may drive a driving voltage to at least one of the plurality of stator coils, thereby inducing a magnetic field that is used to generate a driving torque onto the rotor. The rotor may include the drive axle, and the plurality of static magnets may be attached to the drive axle. A BLDC motor may be more reliable as compared with brushed motors, as oxide layers may be formed on the brushes, which may adversely impact start-up after storage (e.g., over an extended shelf life). Additional advantages of using a BLDC electric motor include lack of rotation when a constant voltage is applied (e.g., commutation is required) which may increase reliability, and the positioning of the rotor and the variation of the rotational speed can be more accurately and precisely controlled.

The rotational speed of the drug delivery device may be controlled by intermittently directing the driving voltage to the plurality of stator coils at a pulse frequency ($f_{puls}$). The driving voltage, in the form of pulses (e.g., sinusoidal waveforms or block waveforms), may be directed to at least one of the plurality of stator coils such that the rotor may be set in rotation due to the driving torque applied with each pulse. Each pulse may correspond to one step of rotation for the electric motor and the rotor may be set in rotation by applying voltage pulses to subsequent stator coils of the plurality of stator coils, or in other words applying commutation. By changing the frequency of the pulses directed to the stator coils, the rotational speed of the rotor may be varied and controlled.

The off-state may be controlled by the control unit directing no driving voltage to the plurality of stator coils, thereby applying no driving torque and stopping or decelerating the rotation of the rotor. The stopping may be defined as a gradual, yet, in some examples, fast deceleration to zero rotation, without active braking and not caused by an adverse event. When no driving voltage is applied to the stator coils, no driving torque may be applied to the magnets forming part of the rotor and consequently the rotor will stop rotating. Optionally, the rotor may rotate a few milliseconds during deceleration due to its moment of inertia, such as for a time period less than 10 milliseconds, or even less than 5 milliseconds in some examples, before decelerating to zero rotation. When no driving voltage is applied for a longer period, for example more than 5 milliseconds, or more than 10 milliseconds in some examples, the rotor may stop rotating completely.

In the on-state, the rotational speed of the electric motor is equal to or above a minimum level for detecting the back-emf signal in the monitoring mode. To fulfill the first requirement (i) mentioned above, the rotational speed of the rotor in the electric motor must be equal to or above the minimum level for measuring and/or detecting a back-emf signal.

In some examples, while in the monitoring mode, no driving voltage may be applied, thereby allowing a voltage measurement unit in the control unit to detect the back-emf signal induced by the rotating rotor in the stator coil of the electric motor.

In some examples, while in the monitoring mode, no driving voltage may be applied by interrupting or pausing (thus not aborting) the driving voltage in the on-state thereby allowing detection of the back-emf signal. The interruption (or pause) may be short (e.g., on the order of milliseconds), such that the rotor rotates, due to its moment of inertia, at the same rotational speed as if a driving voltage is applied.

The driving voltage in the monitoring mode may be interrupted or paused for a time period varying between 0.05 to 2.0 milliseconds. In some examples, the paused time period may be between 0.1 and 1.0 milliseconds. The monitoring for the back-emf signal may be part of a cycle and each cycle includes one monitoring mode where the driving voltage is paused or interrupted for a fraction of the cycle period. The time period for the pausing or interruption may vary between 0.05 and 2.0 milliseconds, followed by applying a driving voltage in the on-state. A subsequent cycle may start when the voltage is paused for the next back-emf measurement.

The electric motor for the delivery device may be modulated in the on/off-state to control the delivery rate by periodically switching the electric motor between the on-state, where the rotational speed of the electric motor is equal to or above the minimum level, and the off-state, where the rotor of the electric motor ceases rotation.

The ratio between the off-state and the on-state (e.g., duty cycle) may be at least 1 to 5, in some examples. In other examples, the ratio may be 1 to 2, 1 to 1, or at least 2 to 1. The ratio may be calculated as the quotient of one time period in the on-state and one time period in the off-state.

The delivery rate or target delivery rate for the medicament may vary between 0.1 ml/min and 10 ml/min, in some examples. In some examples, the delivery rate or the target delivery rate may be between 0.2 ml/min and 5 ml/min or between 0.3 ml/min and 1 ml/min.

The drug delivery device may be included as part of an infusion device, a bolus injector, a patch injector, or an autoinjector. The drug delivery device may be removably carried on the body for example attached to the body using an adhesive. Alternatively, the drug delivery device may be carried by the patient in a holder or strap that can be affixed to the body of the patient. Alternatively, the drug delivery device may be used in a hospital by health care professionals and is not carried or attached to the body, but used as a separate device remote (but still close to) the patient. The medicament may be delivered by the drug delivery device to the patient via an infusion set outside of the drug delivery device, including a tubing that is connectable to the drug delivery device and the tubing ends in a needle for subcutaneous or IV delivery. As an alternative, the medicament may be delivered by an infusion set or fluid path that is located inside the drug delivery device. Such a fluid path may include a skin insertion needle for insertion into the injection site and the skin insertion needle may be driven by a needle insertion mechanism from a retracted position inside the drug delivery device (or inside the housing or housing part of the drug delivery device) to an extended position outside of the drug delivery device. The needle insertion (and retraction) mechanism may be driven by a separate spring or may be driven by the electric motor. The skin insertion needle may be retracted inside the drug delivery device by the needle insertion mechanism after the delivery of the medicament has been completed. Alternatively, a needle shield protects the extended needle after completion of medicament delivery, for example, a cover sleeve surrounding the needle tip extends from the drug delivery device after the medicament has been delivered and/or when the drug delivery device is removed from the skin.

The bolus injector may deliver a volume between 1 ml and 20 ml at once at the delivery ranges mentioned above.

This disclosure further includes embodiments directed to example methods for operating the drug delivery device. An example method may include:

i) Determining a target rotational speed for the electric motor in terms of pulse frequency based on the target delivery rate. A target delivery rate may be preset for the device or selected by a user or a health care professional. The target rotational speed may be determined using the memory of the control unit including a correlation between the target rotational speed and the target delivery rate. The correlation may be based on a generic factory calibration or on a device specific calibration for each device separately or an in-situ calibration during use. The minimum rotational speed for a reliable detection of the back-emf signal may also be stored in the memory of the device.

ii) Comparing the target rotational speed with the minimum rotational speed for detection of the back-emf signal, and (iii) If the target rotational speed is below the minimum rotational speed: Defining a ratio between the on-state and the off-state, where the electric motor may be operated in the on-state at least at the minimum rotational speed and at zero speed in the off-state. The ratio may be selected from a list of ratios in the memory of the device or may be obtained by connecting the drug delivery device to an external database (e.g., stored in an external device, such as a cellular phone), or obtained from a cloud.

If condition (iii) applies: Operating the device in an alternating on/off mode according to the ratio to deliver the fluid medicament through the outlet of the reservoir at the target delivery rate.

However if (iv) the target rotational speed is above the minimum rotational speed for measuring a back-emf signal, then the device may be operated in a continuous mode whereby the electric motor is rotated at the target rotational speed to deliver the fluid medicament through the outlet of the reservoir at the target delivery rate.

Additionally and optionally step (v) may be part of the example method: (v) Selecting an (absolute) on-time period to include a minimum number of rotor revolutions to allow for tracking of deviations. A minimum number a revolutions or steps may be selected to allow reliable detection of rotation of the electric motor, thus also enabling reliable detection of non-rotation of the electric motor due to a) blockage of the drive mechanism as the piston reaches the end of the reservoir or b) due to adverse events, such as an occlusion in the fluid delivery path.

In the example method, the correlation between the target delivery rate (output) and the target rotational speed for the electric motor driving the delivery mechanism (input) may depend on a number of parameters, such as the elasticity of the drive train, the reservoir dimensions, the outlet dimensions of the reservoir, the viscosity of the fluid medicament, the storage or shelf life of the device (including the medicament) and, for a re-usable device, the number of injections or infusions done by the device to account for internal wear. This correlation may be a fixed correlation throughout the lifetime of the device or it may vary or adapt itself to the situation, for example, if a new reservoir is inserted into the device or to account for wear in the device. The device may be "self-learning" in that the correlation stored in the memory is capable to adjust itself (an updated correlation) based on the previously stored correlation.

DETAILED DESCRIPTION

Definitions

The term "medicament" or "medication" may include any flowable medical formulation suitable for controlled administration through a means such as, for example, a cannula or a hollow needle and includes a liquid, a solution, a gel or a fine suspension containing one or more medical active ingredients. A medicament can be a composition including a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The distal end or distal direction is defined by the direction of the needle configured to penetrate the skin of the patient. For an injection pen, this may be the injection needle and the end of the pen holding the needle or being configured to hold the needle is the distal end. For an infusion device the distal end and the distal direction is towards the needle configured to penetrate the skin of the patient, which may be along the axis of the device or tilted or perpendicular to the axis of the device. The distal direction in an infusion device represents the direction in which the medicament flows towards the insertion needle. The proximal direction or end is opposite to the distal direction or end.

Figure 1:
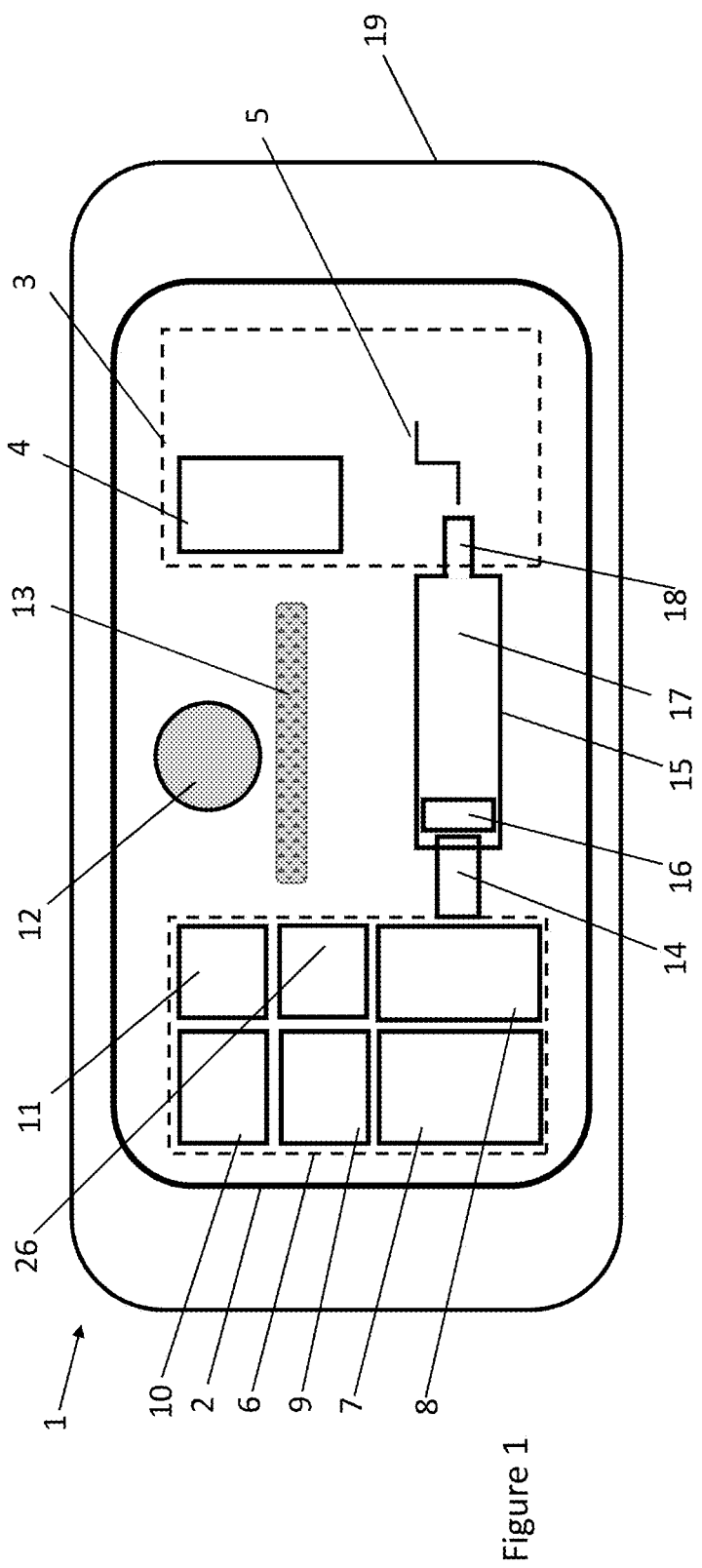
FIG. 1 depicts a top view of an example of a drug delivery device according to the present disclosure.
Figure 2:
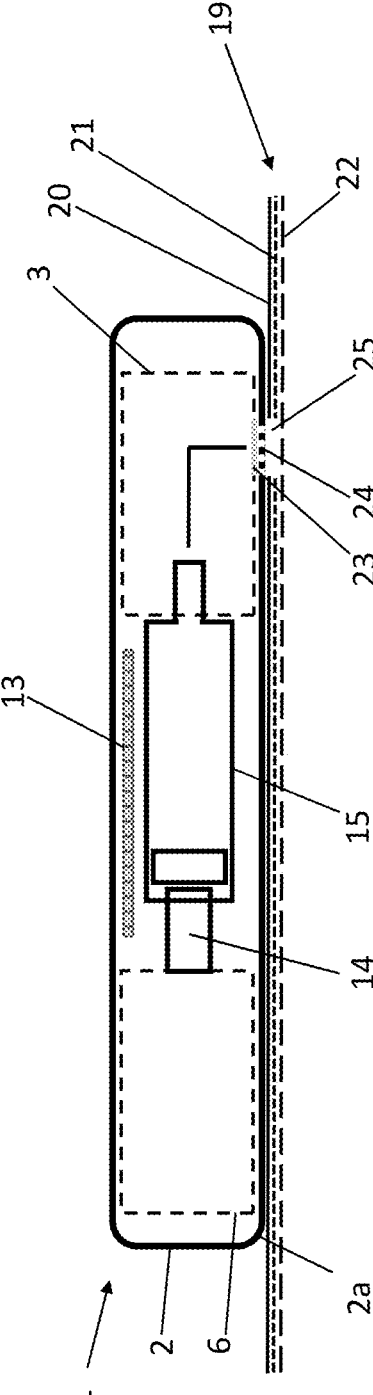
FIG. 2 depicts a longitudinal section of the example of a drug delivery device according to the present disclosure.

FIG. 1 depicts an example of a drug delivery device 1 according to the present disclosure. FIG. 2 depicts a longitudinal section of the example of a drug delivery device according to the present disclosure. The drug delivery device may include a patch injector including a housing 2 providing a wall to separate at least a fluid path unit 3, a delivery unit 6 and a reservoir 15 from the ambient. The housing 2 may have an elongated shape with a bottom housing 2a intended for positioning on, or attachment to, the skin of a patient (FIG. 2). The fluid path unit 3 may include a fluid path 5 having a skin insertion needle (not shown) that is intended to move from inside the housing 2 through an aperture 23 in the fluid path unit into the skin of the patient. The fluid path 5 may include a tubing connecting the skin insertion needle to an outlet 18 of the reservoir 15. The connection between the fluid path 5 and the reservoir 15 may be a permanent connection or the fluid path 5 has a not shown reservoir needle capable of connecting to, or penetrating, the outlet 18 of the reservoir 15. The delivery unit 6 may include an electric motor 7, a gearing 8 that is coupled or connectable to the electric motor 7, a control unit 9 and a battery 26 for powering the device. The battery 26 may be part of the delivery unit 6 or may form a separate unit within the housing 2. The battery 26 powers the control unit 9 and the electric motor 7 for controlling the device and delivery of a medicament 17 though the outlet 18 of the reservoir 15. The control unit 9 controls the rotational speed and on/off state of the electric motor 7 to deliver the medicament 17 at the desired delivery rate. The rotational speed of the electric motor 7 is monitored using a sensor-less system, using the back-emf signal generated at the stator coils of the electric motor 7 during rotation of a rotor. The control unit 9 controls the rotational speed such that a reliable back-emf-signal can be detected, by operating the electric motor 7 at a minimum rotational speed. The electric motor 7 is operated in a monitoring mode for monitoring the rotational speed, where the driving voltage is interrupted or paused for a short period of time such that the back-emf signal can be detected and sent to the control unit. The rotation of the electric motor or a drive shaft connected to the electric motor is transmitted to the gearing 8 which advances a piston rod 14 towards a piston 16 in the reservoir 15. The reservoir includes a glass cartridge closed on one side by the moveable piston 16 and on the opposite side by a pierceable septum forming part of the outlet 18. The piston rod 14 abuts the piston 16 in the cartridge to reduce the volume available for the medicament 17 that is expelled via the outlet 18 through the fluid path 5 into the patient. The delivery unit may furthermore include a transmitter/receiver 10 for wireless communication with an external device such as a smart phone. The transmitter/receiver may be based on Bluetooth®, a low energy Bluetooth®, a NFC, 5G, or a ZigBee® technology. An acoustic signaling system 11 and/or a visual signaling system 13 may be part of the delivery unit 6 or form a separate unit within the housing. The visual signaling 13 may have LED lights located behind the housing 2 or a translucent section within the housing and a plurality of LED lights may signal using different colors. The plurality of LED lights may be arranged along a straight line or a curved line or individual LED lights may form a pattern. A push button 12 may be part of the housing and the user may activate the drug delivery or activate the device by pushing the push button 12.

The drug delivery device 1 may be adapted to be attached to the skin of the patient using an adhesive unit 19 (FIG. 1). The surface area of the adhesive unit 19 may be at least equal to the area of the bottom housing 2a. The adhesive unit 19 may have a larger area and a rim of the adhesive unit 19 surrounds the housing 2 of the drug delivery device 1. The adhesive unit 19 is a multilayered system including a base layer 20 providing support to an adhesive layer 21. The base layer may be a woven or non-woven textile. The adhesive layer 20 is covered by a release liner 22 covering the adhesive. The user removes the release liner 22 by pulling a not shown pull tab or an aperture in the release liner and subsequently attaches the drug delivery device to the skin.

The fluid path unit 3 may form a sterile enclosure surrounding the fluid path unit 5. The sterile enclosure may be formed by a separate housing part located within the housing 2. The fluid path unit 5 includes an aperture 23 for the skin needle. Optionally, the fluid path unit 5 includes a second aperture for the reservoir needle. Both needles may be moved by an insertion mechanism 4. The skin needle may be configured to move from a retracted position, which is within the fluid path unit 3, to an inserted or extended position through the aperture 23 outside of the housing 2, and the reservoir needle may be configured to move from a retracted position within the fluid path unit 3 into the reservoir 15, for example by piercing the septum. The apertures for the skin needle and/or the reservoir needle may be covered by a sealing 24 forming a sterile barrier to protect the fluid path 5 from contamination during storage. The sealing 24 may be formed by a porous membrane such as a Tyvek membrane. Prior to use, the sealing 24 may be removed, or alternatively, the skin needle penetrates through the sealing 24. Removal of the sealing 24 may be separate from removing the release liner 22, or the sealing 24 is removed simultaneously with the release liner 22. The release liner 22 may be attached to the sealing 24 or a coupler, for example, a sticker, may connect the release liner to the sealing 24. Optionally, the release liner 22 forms the sealing 24, for example, a part of the release liner 22 may be heat sealed to the fluid path unit 3. In some examples, the sealing 24 may be separate from the release liner 22 and the base layer 20 and adhesive layer 21 may include an aperture 25 forming a passage for the reservoir needle.

The insertion mechanism 4 may be triggered by the user, for example, by pressing the push button 12 to mechanically release a mechanism (e.g., a latching mechanism), activating the insertion of the skin needle into the skin and/or the reservoir needle into the reservoir 15. Alternatively, the insertion mechanism 4 may be activated by the electric motor 7, for example by rotation in a direction that is opposite to the rotation direction for medicament delivery. The electric motor 7 may directly activate the insertion mechanism 4 or via the gearing 8. The insertion mechanism 4 may be powered by a biasing member, such as a mechanical spring (e.g., a compression or leaf spring), or the insertion itself is powered by the electric motor 7. Optionally, the insertion mechanism 4 includes a skin needle retraction mechanism such that the skin needle may be retracted into the housing 2 after the medicament has been delivered. The drug delivery device 2 may have a skin sensing system, such as a capacitive sensor sensing the proximity of the skin. The skin sensing system may be integrated with the adhesive unit 19 or may be located within the housing 2 or may be part of the bottom housing 2a. The skin sensing system may detect the proximity of the skin (skin attachment) or may detect detachment of the device from the skin. Both skin attachment as well as skin detachment may be signaled to the control unit 9 for activating the device or signaling malfunctioning to the user via the visual and/or acoustic signaling system 13, 11.

Figure 4:
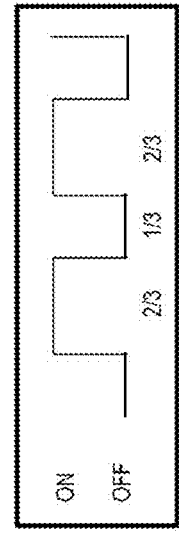
FIG. 4 is a timing diagram depicting modulation of an on/off state of an electric motor according to the present disclosure.
Figure 3:
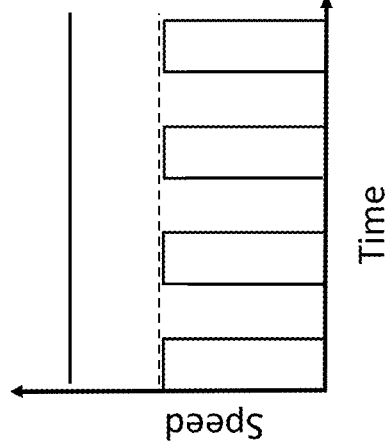
FIG. 3 is a timing diagram depicting changes in rotational speed of an electric motor over time according to the present disclosure.
Figure 5:
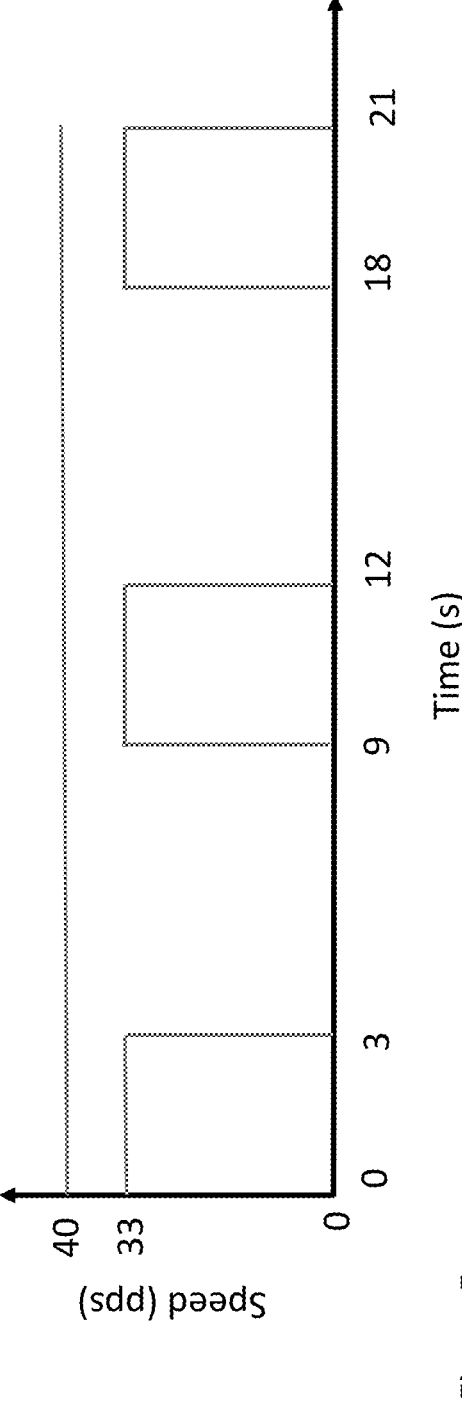
FIG. 5 is a timing diagram depicting changes in rotational speed of an electric motor over time according to the present disclosure.

Example operation and control of the electric motor 7 for the drug delivery device 1 presented above with reference to FIGS. 1 and 2 is presented in FIGS. 3 to 5. In some examples, a brushless DC motor may be used and the pulsed driving voltage may be directed by the control unit 9 to at least one of the plurality of stator coils such that the rotor is set in rotation due to the driving torque applied with each pulse. In some examples, each pulse may correspond to one step of rotation and the rotor is set in rotation by applying voltage pulses to subsequent stator coils of the plurality of stator coils, or in other words, applying commutation. By changing the frequency of the pulses directed to the stator coils, the rotational speed of the rotor may be controlled. The rotational speed of the rotor (e.g., revolutions/s) may linearly correlate with the pulse frequency in pulses per second (pps).

FIG. 3 is a timing diagram depicting changes in rotational speed of an electric motor over time according to the present disclosure. In FIG. 3, the rotational speed is shown as a function of time. If the rotational speed that is required for a desired delivery rate is above the minimum level for detecting a reliable back-emf signal, then the control unit ensures that the electric motor is running continuously in the on-state (e.g., represented by a solid horizontal line in FIG. 3). In the example depicted in FIG. 3, during the on-state the rotor rotates and the driving voltage is interrupted in the monitoring mode for a time period (e.g., 0.5 milliseconds) to allow for measuring the back-emf signal.

If the delivery rate or the targeted delivery rate is lower, and this may result in operation of the electric motor at a target rotational speed below the minimum level for reliable back-emf detection (shown as the dotted line), then the control unit may switch the electric motor between the on-state, where the rotational speed is sufficient for detecting a reliable back-emf signal in the monitoring mode, and the off-state where the driving voltage is interrupted for a longer period of time such that the rotor stops rotating. By modulation of the on and off-time, the medicament can be delivered at the desired or targeted (low) volumetric delivery rate without compromising the sensorless detection of the rotational speed for rotor in the electric motor. FIG. 4 is a timing diagram depicting modulation of an on/off state of an electric motor according to the present disclosure. In the example depicted in FIG. 4, the electric motor is controlled such that it is for ⅔ of the time in the on-state and for ⅓ of the time in the off-state. It is appreciated that the on-off duty cycle depicted in FIG. 4 is exemplary, and other on/off duty cycles may be implemented without departing from the scope of the disclosure.

A more detailed calculation for the modulation is presented in the following. The targeted rotational speed is expressed in pulses per seconds (pps) and, in this example, a minimum level of $V_{min}$=33 pps is required for detection of reliable back-emf signal. This may correspond to the minimum rotational speed for back-emf detection. There may also be a minimum number of steps required (each pulse corresponds to one step) for detecting changes in rotation. Such a change in rotation can be due to mechanical blockage in the gearing mechanism or an occlusion within the fluid path. Such blocking may need a certain number of steps to be recorded prior to blockage to ensure a reliable detection of a rotating rotor. The minimum steps may depend on the sensitivity of the system. For this specific, non-limiting example, the minimum number of steps is $S_{min}$=100 steps.

The on-time ($t_{on}$) may be calculated as:

$$t_{on} = S_{min}/V_{min}$$

In this example, the on-time is 3 seconds.

The percentage of the time where the device is operated in the on-state ($on_\%$) may be calculated as the ratio between the target delivery rate ($V_{target}$) and the minimum detection speed ($V_{min}$):

$$on_\% = V_{target}/V_{min}$$

If the desired or targeted delivery rate $V_{target}$ (volumetric) corresponds to a target rotational speed in terms of a pulse frequency of 11 pps, then the device is operated for 11/33 is 33% ($on_\%$) of the time in the on-state (for 3 seconds, $t_{on}$).

The percentage of the time where the device is operated in the off-state ($off_\%$) is calculated as:

$$off_\% = 1-on_\%$$

And the ratio between the on-state and the off-state ($R_{on/off}$) where the device is operated in the on-state is calculated as:

$$R_{on/off} = V_{target}/V_{min}/(1-V_{target}/V_{min})$$

For the current example, the on/off ratio is thus 1:2. And the off time can be calculated as:

$$t_{off} = t_{on}/R_{on/off}$$

FIG. 5 is a timing diagram depicting changes in rotational speed of an electric motor over time according to the present disclosure. In this example, the device is thus operated for 3 seconds in the on-state and for 6 seconds in the off-state, which is presented in FIG. 5.

If the targeted delivery rate corresponds to a pulse frequency of 40 pps (e.g. above the minimum level of 33 pps for back-emf detection) then the device is continuously operated in the "on" state. See FIG. 5. It is appreciated that the specific pps and time values and the on-off duty cycle depicted in FIG. 5 are exemplary, and other pps and time values and on/off duty cycles may be implemented without departing from the scope of the disclosure.

Variations on the voltage modulation can easily be calculated. For example for a more sensitive system, it may take $S_{min}$=66 steps for a reliable detecting of rotation and in that case, with a minimum speed level $V_{min}$=33 pps for back-emf detection, it may take 66/33=2 seconds rotation at 33 pps. If the required delivery rate corresponds to 22 pps, then the control unit operates the device for 2 seconds in the on-state and for 1 second in the off-state. Thus, an interval operation where ⅔ of the time the device is in the on-state, as shown in FIG. 4.

In the claims, the word "comprising" does not exclude other elements or steps, and the indefinite article "a" or "an" does not exclude a plurality. For example "a control unit" does not exclude the fact that there may be two control units that functionally or structurally fulfill the purpose of "a control unit".

LIST OF REFERENCE SIGNS

1 Drug delivery device
2 Housing
2a Bottom housing
3 Fluid path unit
4 Insertion mechanism 17 Medicament
5 Fluid path
6 Delivery unit
7 Electric motor
8 Gearing
9 Control unit
10 Transmitter/receiver
11 Acoustic signaling
12 Push button
13 Optical signaling (LED)
14 Piston rod
15 Reservoir
16 Piston
18 Outlet
19 Adhesive unit
20 Base layer
21 Adhesive layer
22 Release liner
23 Aperture fluid path unit
24 Sealing
25 Aperture base layer/adhesive layer
26 Battery

What is claimed is:

1. A drug delivery device including
a reservoir configured to contain a fluid medicament to be delivered by advancing a piston in the reservoir at an advancement speed defining a delivery rate for the medicament through an outlet of the reservoir,
an electric motor configured to drive a delivery mechanism by rotation to advance the piston,
a control unit configured to control a rotational speed and an on state and an off state of the electric motor,
wherein the control unit is configured to determine the rotational speed based on a back-electromagnetic force (back-emf) signal provided from the electric motor while the electric motor is operating in a monitoring mode,
wherein the control unit is configured to control the rotational speed of the electric motor to be, while in the on state, above a minimum speed such that a back-emf signal can be detected in the monitoring mode, and wherein the control unit is configured to modulate the on state and the off state of the electric motor to adjust the delivery rate to a target delivery rate,
wherein the delivery rate varies between 0.1 ml/min and 10 ml/min.

2. The drug delivery device of claim 1, wherein the delivery mechanism comprises a piston rod that abuts the piston in the reservoir, and wherein the piston rod is advanced at the advancement speed by the delivery mechanism.

3. The drug delivery device of claim 2, wherein the reservoir includes a cartridge comprising the piston that is configured to be linearly advanced in the cartridge by the delivery mechanism towards an outlet of the cartridge.

4. The drug delivery device of claim 1, wherein the rotational speed of the electric motor in the on state is equal to or above a minimum level for detecting the back-emf signal in the monitoring mode.

5. The drug delivery device of claim 1, wherein the device includes an infusion device, a bolus injector, a patch injector, an on body delivering system, or an autoinjector.

6. A drug delivery device including
a reservoir configured to contain a fluid medicament to be delivered by advancing a piston in the reservoir at an advancement speed defining a delivery rate for the medicament through an outlet of the reservoir,
an electric motor configured to drive a delivery mechanism by rotation to advance the piston,
a control unit configured to control a rotational speed and an on state and an off state of the electric motor,
wherein the control unit is configured to determine the rotational speed based on a back-electromagnetic force (back-emf) signal provided from the electric motor while the electric motor is operating in a monitoring mode,
wherein the control unit is configured to control the rotational speed of the electric motor to be, while in the on state, above a minimum speed such that a back-emf signal can be detected in the monitoring mode, and wherein the control unit is configured to modulate the on state and the off state of the electric motor to adjust the delivery rate to a target delivery rate,
wherein the delivery mechanism comprises a piston rod that abuts the piston in the reservoir, and wherein the piston rod is advanced at the advancement speed by the delivery mechanism,
wherein the reservoir includes a cartridge comprising the piston that is configured to be linearly advanced in the cartridge by the delivery mechanism towards an outlet of the cartridge, and
wherein the electric motor includes a brushless direct-current (DC) motor, and wherein the control unit is configured to control the on state by providing a driving voltage to a stator coil of the DC motor, wherein provision of the driving voltage to the stator coil of the DC motor is configured to cause application of a driving torque to a rotor of the DC motor to cause rotation of the rotor.

7. The drug delivery device of claim 6, wherein the control unit is configured to control the rotational speed by intermittently providing the driving voltage to the stator coil based on a pulse frequency.

8. The drug delivery device according to claim 7, wherein the control unit is configured to control the off state by stopping provision of the driving voltage to the stator coil, wherein, in response to the control unit stopping provision of the driving voltage to the stator coil, rotation of the rotor of the DC motor is stopped.

9. The drug delivery device of claim 6, wherein, while in the monitoring mode, the control unit is configured to stop provision of the driving voltage to the stator coil of the DC motor and a voltage measurement unit of the control unit is configured to detect the back-emf signal induced in the stator coil caused by rotation of the rotor of the DC motor while the control unit has stopped provision of the driving voltage.

10. The drug delivery device of claim 9, wherein, while in the monitoring mode, the control unit is configured to stop provision of the driving voltage by interrupting the driving voltage in the on state to allow detection of the back-emf signal.

11. The drug delivery device of claim 10, wherein the control unit is configured to interrupt the driving voltage for a time period selected from times including and between 0.05 to 2.0 milliseconds.

12. The drug delivery device of claim 10, wherein the control unit is configured to modulate the on state and the off state of the electric motor to control the delivery rate by periodically switching the electric motor between the on state where the rotational speed of the electric motor is equal to or greater than a minimum level for detecting the back-emf signal in the monitoring mode, and the off state where a rotor of the electric motor stops rotation.

13. The drug delivery device of claim 12, wherein a ratio between the on state and the off state is 1 to 5.

14. A method, comprising:

using a control unit to determine a rotational speed of an electric motor of a drug delivery device based on a back-electromagnetic force (back-emf) signal provided from the electric motor while the electric motor is operating in a monitoring mode;

determining, using the control unit, a target rotational speed for the electric motor in terms of pulse frequency based on a target delivery rate for delivery of a fluid medicament through an outlet of a reservoir of the drug delivery device;

comparing, using the control unit, the target rotational speed with a minimum rotational speed detected by the control unit as the back-emf signal of the electric motor while the electric motor is operating in the monitoring mode;

in response to the target rotational speed being less than the minimum rotational speed, using the control unit to:

define a ratio between an on state and an off state such that the electric motor is operated in the on state at the minimum rotational speed and at zero speed in the off state;

cause the electric motor to operate in an alternating fashion to modulate between the on state and the off state based on the ratio in order to drive a delivery mechanism and cause advancement of a piston of the drug delivery device, wherein advancement of the piston is configured to cause the fluid medicament to be delivered at the outlet of the reservoir at a delivery rate that is based on the target delivery rate; and in response to the target rotational speed being equal to or greater than the minimum rotational speed, using the control unit to:

cause the electric motor to operate continuously in the on state at the target rotational speed in order to drive the delivery mechanism and cause advancement of the piston of the drug delivery device, wherein advancement of the piston is configured to cause the fluid medicament to be delivered at the outlet of the reservoir at the delivery rate that is based on the target delivery rate, wherein the delivery rate varies between 0.1 ml/min and 10 ml/min.

* * * * *